US011219657B2

(12) United States Patent
Lecozannet et al.

(10) Patent No.: US 11,219,657 B2
(45) Date of Patent: Jan. 11, 2022

(54) METHOD FOR TREATING OR PREVENTING INFLAMMATION

(71) Applicant: NATUREX SA, Avignon (FR)

(72) Inventors: Romain Lecozannet, Montfavet (FR); Pascale Elizabeth Renee Fanca-Berthon, Le Thor (FR); Leila Denise Falcao, Avignon (FR); Matthieu Tenon, Avignon (FR); Antoine Charles Bily, Vedene (FR); Marc Roller, Morieres les Avignon (FR); Nicolas Feuillere, Courthezon (FR); Simona Birtic, Cavaillon (FR)

(73) Assignee: Naturex SA, Avignon (FR)

( * ) Notice: Subject to any disclaimer, the term of this patent is extended or adjusted under 35 U.S.C. 154(b) by 0 days.

(21) Appl. No.: 16/472,088

(22) PCT Filed: Dec. 21, 2017

(86) PCT No.: PCT/EP2017/084266
§ 371 (c)(1),
(2) Date: Jun. 20, 2019

(87) PCT Pub. No.: WO2018/115381
PCT Pub. Date: Jun. 28, 2018

(65) Prior Publication Data
US 2020/0222486 A1 Jul. 16, 2020

(30) Foreign Application Priority Data
Dec. 23, 2016 (GB) .................................... 1622161

(51) Int. Cl.
| A61K 36/73 | (2006.01) |
| A23K 10/30 | (2016.01) |
| A23L 33/105 | (2016.01) |
| A61P 19/02 | (2006.01) |
| A61P 29/00 | (2006.01) |

(52) U.S. Cl.
CPC .............. *A61K 36/73* (2013.01); *A23K 10/30* (2016.05); *A23L 33/105* (2016.08); *A61P 19/02* (2018.01); *A61P 29/00* (2018.01); *A23V 2002/00* (2013.01)

(58) Field of Classification Search
None
See application file for complete search history.

(56) References Cited

U.S. PATENT DOCUMENTS

2016/0095890 A1* 4/2016 Stancioiu ........... A61K 2300/00
424/539

FOREIGN PATENT DOCUMENTS

| CN | 104306517 A | 1/2015 |
| CN | 1042888428 A | 1/2015 |
| CN | 104829737 | * 8/2015 |
| KR | 20010067023 A | 7/2001 |
| KR | 10-2003-0015654 | * 2/2003 |
| KR | 2003 0015654 A | 2/2003 |
| KR | 101287021 B1 | 7/2013 |
| WO | 2003/074067 A1 | 9/2003 |
| WO | 2005/000330 A1 | 1/2005 |

OTHER PUBLICATIONS

Jean-Giles, D. et al. Anti-inflammatory Effects of Polyphenolic Enriched Red Raspberry Extract in an Antigen Induced Arthritis Rat Model. J of Agricultural and Food Chemistry 60(23)5755-5762, Jun. 2012. (Year: 2012).*
Daglia, M. et al. Plant and Fungal Food Components with Potential Activity on the Development of Microbial Oral Diseases. J of Biomedicine and Biotechnology vol. 2011 ID 274578, 1-9 2011. (Year: 2011).*
Luo, T. et al. Phytochemical Composition and Potential Biological Activities Assessment of Raspberry Leaf Extracts from Nine Different Raspberry Species and Raspberry Leaf Tea. J of Berry Research 10(2)295-309, 2020. (Year: 2020).*
International Search Report and Written Opinion for corresponding Application No. PCT/EP2017/084266 (dated Apr. 20, 2018).
Vickers et al., "Raspberry Leaf Herbal Extract Significantly Reduces Pain and Inflammation in Oral Lichen Planus Patients—A Case Series Analysis," Open J. Dentist. Oral Med. 3(1):73-81 (2015).
Pashinskiy et al., "Anti-Inflammatory Activity of Rubus idaeus (Rosaceae) Leaves Infusion," Database Biosis, Biosciences Information Service: Philadelphia, PA (2008).
Figueira et al., "Chemical Characterization of a Red Raspberry Fruit Extract and Evaluation of its Pharmacological Effects in Experimental Models of Acute Inflammation and Collagen-Induced Arthritis," Food & Function 5(12):3241-3251 (2014).
Jean-Gilles et al., "Anti-Inflammatory Effects of Polyphenolic-Enriched Red Raspberry Extract in an Antigen-Induced Arthritis Rat Model," J. Agrricult. Food Chem. 60(23):5755-5762 (2012).
Sangiovanni et al., "Ellagitannins from Rubus Berries for the Control of Gastric Inflammation: In Vitro and In Vivo Studies," PLOS One 8(8):e71762 (2013).

* cited by examiner

Primary Examiner — Ralph J Gitomer
(74) Attorney, Agent, or Firm — Curatolo Sidoti Co., LPA; Salvatore A. Sidoti

(57) ABSTRACT

The present invention relates to an extract obtained from or obtainable from *Rubus idaeus*, a composition comprising an extract obtained from or obtainable from *Rubus idaeus*, processes for providing such an extract, and methods and uses relating to such extracts. In particular, the present invention relates to an extract or composition for use in treating or preventing inflammation, such as arthritis and joint inflammation.

12 Claims, 7 Drawing Sheets

METHOD FOR TREATING OR PREVENTING INFLAMMATION

This application is a national stage application under 35 U.S.C. § 371 of PCT Application No. PCT/EP2017/084266, filed Dec. 21, 2017, which claims the priority benefit of Great Britain Patent Application No. 1622161.6, filed Dec. 23, 2016.

The present invention relates to an extract obtained from or obtainable from *Rubus idaeus*, a composition comprising an extract obtained from or obtainable from *Rubus idaeus*, processes for providing such an extract, and uses of such extracts. In particular, the present invention relates to an extract or composition for use in treating or preventing inflammation, such as arthritis and joint inflammation.

The listing or discussion of an apparently prior-published document in this specification should not necessarily be taken as an acknowledgement that the document is part of the state of the art or is common general knowledge.

Inflammation is a complex biological response of tissues to harmful stimuli, such as pathogens, tissue damage, or irritants. It is a protective attempt by the tissue to remove the injurious stimuli as well as initiate the healing process for the tissue.

In a typical inflammation response, a cascade of biochemical events propagates and matures the inflammation response. Circulating peripheral blood mononuclear cells (PBMCs) such as leukocytes are important cells in these biochemical cascades. These cells express a range of pathogen-recognition receptors (PRRs) which recognize highly conserved pathogen-associated molecular patterns (PAMPs) present with bacteria, viruses, fungi, mycoplasma, and parasitic protozoa.

Several biochemical molecules may be involved with inflammation or an immune response. For example, tumor necrosis factor-alpha (TNF-α) is a cytokine involved in systemic inflammation and is used in the initiation of inflammation. Various interleukins may also be involved such as interleukin 8 (IL-8), which is a chemoattractant for certain inflammatory molecules and induces chemotaxis in its target cells, interleukin 4 (IL-4), which induces differentiation of naïve helper T cells to Th2 cells and the stimulation of B-cells, interleukin 2 (IL-2), which is a cytokine that attracts lymphocytes or leukocytes, interleukin 6 (IL-6), which is a cytokine involved in acute phase protein synthesis and the production of neutrophils in the bone marrow, interleukin 10 (IL-10) which is an anti-inflammatory cytokine and interleukins-1 alpha (IL-1α) and beta (IL-1β), which are cytokines involved in the initial production of inflammation.

Abnormalities associated with inflammation comprise a large, unrelated group of disorders which underlie a variety of human diseases (inflammatory disorders). Examples of diseases with an inflammatory aspect include (but are not limited to) asthma, autoimmune disease, glomerulonephritis, allergy (hypersensitivities), inflammatory bowel diseases, reperfusion injury, arthritis, tumors, neurological inflammation and transplant rejection.

The term "inflammation" as used herein, may refer to acute inflammation and/or chronic inflammation.

Attempts to treat inflammation have met with limited success. This is due, in part, to the fact that the etiology of inflammation is a complex response based in part on the various inflammation inducing molecules and the multitude of inflammation mediating and sensitizing molecules that appear to elicit inflammation via redundant mechanism.

Many anti-inflammatory drugs currently in use, also inhibit regulatory loops that release endogenous anti-inflammatory molecules. For example, NSAIDs reduce inflammation by blocking the enzymatic activity of cyclooxygenase, a key enzyme that catalyzes the conversion of arachidonic acid to prostaglandins and leukotrienes. Thus, NSAIDs reduce inflammation by preventing the synthesis of all prostaglandins. However, NSAIDs not only prevent the synthesis of proinflammatory prostaglandins, these compounds also prevent the synthesis of anti-inflammatory prostaglandins. Hence, NSAIDs have limited success as they block endogenous anti-inflammatory response, which in some instances may prolong chronic inflammation. Therefore, compounds, compositions, uses, and methods preferentially inhibiting pro-inflammatory responses would be highly desirable for the treatment of inflammation.

The present inventors have surprisingly and unexpectedly found that extracts obtained from *Rubus idaeus*, such as from the leaves of *Rubus idaeus*, possess potent anti-inflammatory activity, including activity which reduces and/or inhibits the release of at least one proinflammatory cytokine. These effects suggest that extracts obtained from *Rubus idaeus*, such as from the leaves of *Rubus idaeus*, may have numerous therapeutic and non-therapeutic uses (e.g. cosmetic uses), such as treating or preventing inflammation.

DETAILED DESCRIPTION OF THE INVENTION

Figure 1:
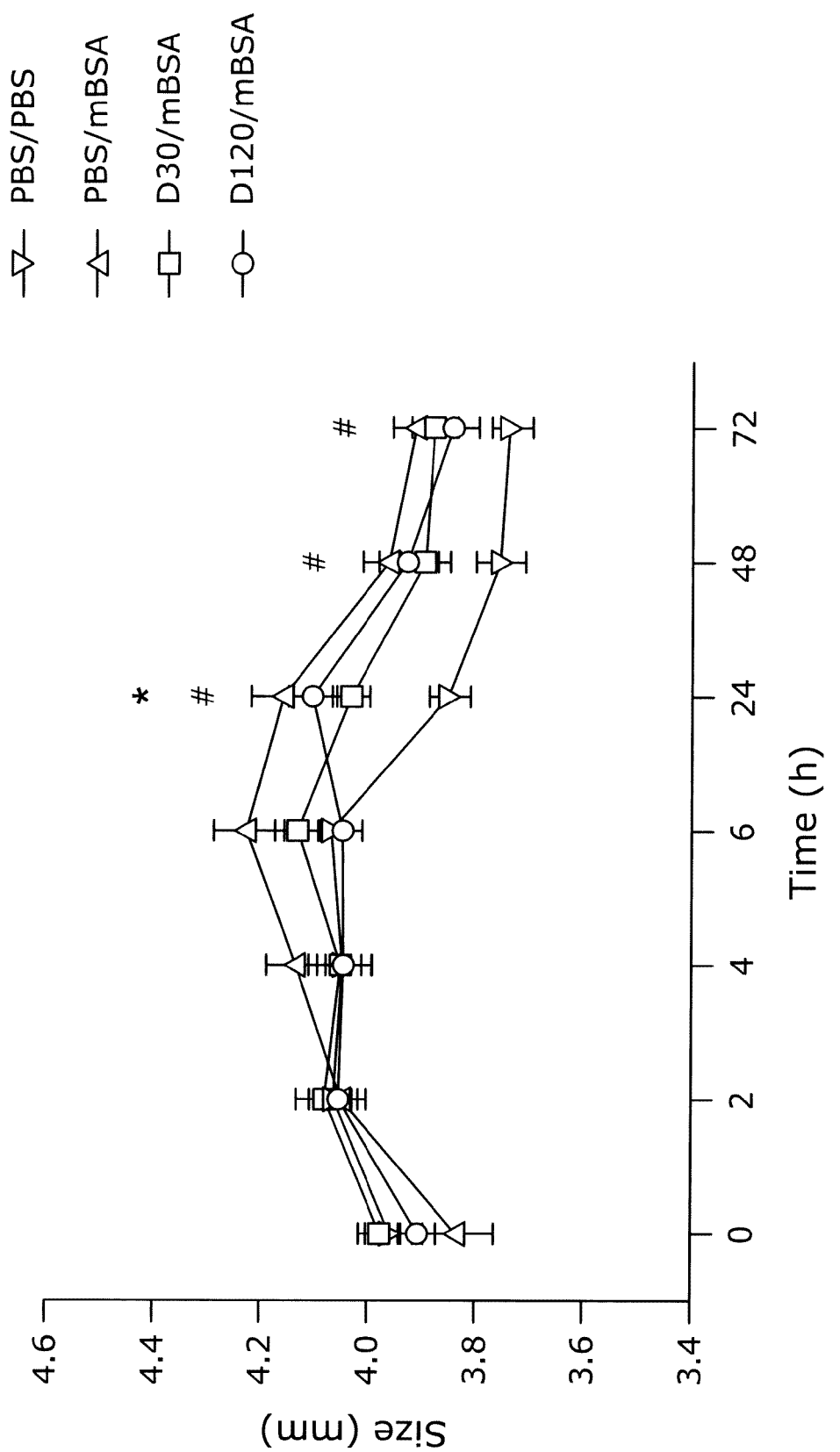
FIG. 1 depicts the paw thickness of the treated animals based on the procedure detailed in Example 4. $P<0.05$ for PBS/mBSA vs D120/mBSA; #$P<0.05$ for PBS/PBS vs. PBS/mBSA.

According to the present invention, there is provided an extract obtained from or obtainable from *Rubus idaeus*. For example, the extract may be obtained from or obtainable from *Rubus idaeus* in the absence of other plants of the *Rubus* species. This extract may be referred to hereinafter as the "extract of the invention".

Typically, the extract of the invention may be an extract obtained from or obtainable from *Rubus idaeus*, in particular from the aerial part of the plant, such as the stems and/or leaves. For instance, in some aspects, the extract of the invention may not be obtained from or obtainable from the seeds and/or fruit of *Rubus idaeus*. For example, the extract may be obtained from or obtainable from the leave of *Rubus idaeus* only.

As will be appreciated by the person skilled in the art, as used herein the term "obtainable from" means that the extract may be obtained from a plant or may be isolated from the plant, or may be obtained from an alternative source, for example by chemical synthesis or enzymatic production. Whereas the term "obtained" as used herein, means that the extract is directly derived from the plant source.

The extract obtained from or obtainable from *Rubus idaeus* may be an aqueous extract, an alcohol extract or an organic extract. In some instances, an aqueous extract obtained from *Rubus idaeus* and an alcohol extract obtained from *Rubus idaeus* may be combined to form a mixed *Rubus idaeus* extract. The ratio of aqueous extract to alcohol extract in the mixed *Rubus idaeus* extract may be from 20:1 to 1:20 or from 1:10 to 10:1, such as from 1:5 to 5:1.

The term "aqueous extract" as used herein, refers to the extract obtained from *Rubus idaeus* when the extraction from the plant (such as the aerial part of plant, for example the leaves) has been performed using water as the only solvent.

The term "alcohol extract" as used herein, refers to the extract obtained from *Rubus idaeus* when the extraction from the plant (such as the aerial part of plant, for example the leaves) has been performed using an alcohol as the solvent. The alcohol solvent may consist of only alcohol (e.g. 100% alcohol), for example 100% ethanol, or may be a mixture of an alcohol and water (hydro-alcoholic solvent), for example, a mix of ethanol and water (hydro-ethanolic solvent), for example, from about 1% to about 99% alcohol (e.g. ethanol) in water. In some instances, the alcohol solvent may comprise or consist of from about 30% ethanol to about 70% ethanol, i.e. have a ratio of ethanol/water of from about 30/70 to about 70/30 v/v. Where the extract has been obtained using a hydro-alcoholic solvent it is typically referred to as the hydro-alcoholic extract.

The term "organic extract" as used herein, refers to the extract obtained from *Rubus idaeus* when the exaction from the plant (such as the aerial part of the plant) has been performed using an organic solvent that is not an alcohol as the solvent. For example, the organic solvent may be selected from the group consisting of acetic acid, acetone, acetonitrile, benzene, 1-butanol, 2-butanol, 2-butanone, carbon tetrachloride, chlorobenzene, chloroform, cyclohexane, 1,2-dichloroethane, diethylene glycol, diethyl ether, diglyme (diethylene glycol, dimethyl ether), 1,2-dimethoxy-ethane (glyme, DME), dimethyl-formamide (DMF), dimethyl sulfoxide (DMSO), 1,4-dioxane, ethyl acetate, ethylene glycol, glycerin, heptane, hexamethylphosphoramide (HMPA), hexamethylphosphorous, triamide (HMPT), hexane, methyl t-butyl, ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene and p-xylene.

For example, the extract of the invention may be a hydro-ethanolic extract obtained or obtainable from the leaves of *Rubus idaeus*.

The extract obtained from *Rubus idaeus* may comprise:
(i) from about 1% to about 40% by weight of the extract, such as from about 2% to about 20% or from about 2% to about 15% by weight of phenolic compounds including from about 1% to about 10% by weight of the extract, such as from about 2% to about 8% by weight of the extract sanguiin H6;
(ii) from about 0.5% to about 7% by weight of the extract, such as from about 1% to about 4% by weight of the extract of hydroxycimmanic acid and ellagic compounds; and
(iii) from about 1% to about 15% by weight of the extract, such as from about 2% to about 6% by weight of the extract of flavonoid compounds.

For example, the aqueous extract obtained from *Rubus idaeus* may comprise:
(i) from about 1.5% to about 40% by weight of the extract, such as from about 2.5% to about 15% or from about 2.5% to about 10% by weight of the extract of phenolic compounds;
(ii) from about 0.5% to about 6% by weight of the extract, such as from about 1% to about 1.5% by weight of the extract of hydroxycimmanic acid and ellagic compounds; and
(iii) from about 1% to about 15% by weight of the extract, such as from about 2% to about 6% by weight of the extract of flavonoid compounds.

For example, the ethanol extract obtained from *Rubus idaeus*, such as from a 30% alcohol extract, may comprise:
(i) from about 1% to about 40% by weight of the extract, such as from about 7.5% to about 20% or from about 10% to about 15% by weight of the extract of phenolic compounds including from about 1% to about 10% by weight of the extract, such as from about 2% to about 8% by weight of the extract sanguiin H6;
(ii) from about 0.5% to about 7% by weight of the extract, such as from about 1% to about 4% by weight of the extract of hydroxycimmanic acid and ellagic compounds; and
(iii) from about 1% to about 15% by weight of the extract, such as from about 2.5% to about 6% by weight of the extract of flavonoid compounds.

The extract obtained from *Rubus idaeus* may also comprise total polyphenols in an amount from about 10% to about 30%, such as from about 15% to about 25% by weight of the extract as calculated using the Folin Ciocalteu method.

Phenolic compounds in the extract obtained from *Rubus idaeus* include, but are not limited to, compounds from the ellagitannin family, geraniin, sanguiin H10, lambertianin C and sanguiin H6.

In a particular instance, the extract of the invention is a hydro-ethanolic extract (such as a hydro-ethanolic extract obtained using ethanol/water in a ratio of from about 30/70 to about 70/30 v/v) from the leaves of *Rubus idaeus*. It has been surprisingly found by the present inventors that such an extract contains advantageous combinations of certain active compounds.

For example, a hydro-ethanolic extract of the invention as previously defined has been found to contain high concentrations (such as greater than 0.2%, or greater than 0.4%) of sanguiin H6, which has been found to have Granzyme B inhibition, which has been found to be involved in conditions such as rheumatoid arthritis and/or osteoarthritis.

Hydroxycimmanic acid and ellagic compounds in the extract obtained from *Rubus idaeus* include, but are not limited to, chlorogenic acid, p-coumaric acid and ellagic acid.

Flavonoid compounds in the extract obtained from *Rubus idaeus* include, but are not limited to, quercetin-3-O-xyl-glucuronide, hyperoside, kaempferol glucoside, quercetin-3-O-glucuronide, quercetin ($C_{27}H_{28}O_{16}$), kaempferol, kaempferol-3-O-glucuronide and kaempferol-3-O-galactoside.

Unless otherwise stated herein, the weight percentages listed are based on the total weight of extract obtained either in dry or liquid form. For example, in some aspects, the weight percentages listed are based on the total weight of the dry extract.

For the avoidance of doubt, preferences, options, particular features and the like indicated for a given aspect, feature or parameter of the invention should, unless the context indicates otherwise, be regarded as having been disclosed in combination with any and all other preferences, options particular features and the like as indicated for the same or other aspects, features and parameters of the invention.

The term "about" as used herein, e.g. when referring to a measurable value (such as an amount or weight of a particular component in the reaction mixture), refers to variations of ±20%, ±10%, ±5%, ±1%, ±0.5%, or, particularly, ±0.1% of the specified amount.

The skilled person will understand that the extract of the invention may be provided in solid form or in liquid form. By solid form, it is included that the extract may be provided as an amorphous solid, or as a crystalline or part-crystalline solid.

Compositions and Administration

The extract of the invention may be provided in the form of a pharmaceutical composition (which may also be referred to as a pharmaceutical formulation), veterinary composition or functional food composition, such as a food, feed or pet food or a food, feed or pet food supplement, comprising the extract of the invention and optionally a pharmaceutically or veterinary acceptable excipient or (functional) food acceptable ingredient, as appropriate.

Typically, the extract of the invention is provided in a composition in the absence of other plant extracts. For example, in the absence of extracts obtained from or obtainable from other *Rubus* species and/or other berry extracts, such as extracts obtained from or obtainable from blueberry, blackberry, asaiberry, raspberry, bilberry, cranberry, black chokeberry, (Aronia fruit), sesame fruit, shopberry and strawberry.

As used herein, references to pharmaceutically or veterinary acceptable excipients may refer to pharmaceutically or veterinary acceptable adjuvants, diluents and/or carriers as known to those skilled in the art.

Food acceptable ingredients include those known in the art (including those also referred to herein as pharmaceutically acceptable excipients) and can be natural or non-natural, i.e. their structure may occur in nature or not. In certain instances, they can originate from natural compounds and be later modified (e.g. maltodextrin).

By "pharmaceutically or veterinary acceptable" we mean that the additional components of the composition are generally safe, non-toxic, and neither biologically nor otherwise undesirable. For example, the additional components are generally sterile and pyrogen free. Such components must be "acceptable" in the sense of being compatible with the extract of the invention and not deleterious to the recipients thereof. Thus, "pharmaceutically acceptable excipients" includes any compound(s) used in forming a part of the formulation that is intended to act merely as an excipient, i.e. not intended to have biological activity itself.

The skilled person will understand that extracts of the invention (e.g. in the form of compositions, such as pharmaceutical or veterinary compositions) may be administered to a patient or subject (e.g. a human or animal patient or subject) by any suitable route, such as by the oral, rectal, nasal, pulmonary, buccal, sublingual, transdermal, intracisternal, intraperitoneal, and parenteral (including subcutaneous, intramuscular, intrathecal, intravenous and intradermal) route.

In particular, extracts of the invention may be administered orally. In such instances, pharmaceutical or veterinary compositions according to the present invention may be specifically formulated for administration by the oral route.

Pharmaceutical or veterinary compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art.

Liquid dosage forms for oral administration include solutions, emulsions, aqueous or oily suspensions, syrups and elixirs.

Compositions (e.g. pharmaceutical or veterinary or food compositions) described herein, such as those intended for oral administration, may be prepared according to methods known to those skilled in the art, such as by bringing the components of the composition into admixture.

The compositions of the invention may contain one or more additional components as food ingredients or pharmaceutical components, such as sweetening agents, flavouring agents, colouring agents and preserving agents. The compositions of the invention may contain the active ingredient(s) in admixture with non-toxic pharmaceutically acceptable excipients (or ingredients) which are suitable for the manufacture of tablets. These excipients (or ingredients) may, for example, be: inert diluents, such as calcium carbonate, sodium carbonate, lactose, calcium phosphate or sodium phosphate; granulating and disintegrating agents, for example, corn starch, maltodextrin or alginic acid; binding agents, for example, starch, gelatine or acacia; and lubricating agents, for example magnesium stearate, stearic acid or talc.

The compositions of the invention may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Suitable pharmaceutical or veterinary carriers include inert solid diluents or fillers, sterile aqueous solutions and various organic solvents. Examples of solid carriers are lactose, terra alba, sucrose, cyclodextrin, maltodextrin, dextrin, talc, gelatine, agar, pectin, acacia, magnesium stearate, magnesium hydroxide; stearic acid, arabic gum, modified starch and lower alkyl ethers of cellulose, saccharose, silicon dioxide. Examples of liquid carriers are syrup, vegetables oils, phospholipids, fatty acids, fatty acid amines, polyoxyethylene and water. Moreover, the carrier or diluent may include any sustained release material known in the art, such as glyceryl monostearate or glyceryl distearate, alone or mixed with a wax.

Moreover, the carrier or diluent may include any sustained release material known in the art, such as glyceryl monostearate or glyceryl distearate, alone or mixed with a wax.

The term "carrier" as used herein, may refer to a natural product or a product originating from nature that has been transformed or modified so that it is distinct from the natural product from which it originated.

In an aspect of the invention, the extract of the invention is provided in a composition comprising maltodextrin and/or silicon dioxide.

Depending on the disorder, and the subject, to be treated, as well as the route of administration, extracts of the invention may be administered at varying doses (i.e. therapeutically effective doses, as administered to a patient in need thereof). In this regard, the skilled person will appreciate that the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease.

The pharmaceutical or veterinary or food compositions may comprise an extract obtained from or obtainable from *Rubus idaeus* in a therapeutically effective amount. As used herein, the term "effective amount" is synonymous with "therapeutically effective amount", "effective dose", or "therapeutically effective dose" and when used in reference to treating inflammation refers to the minimum dose of the extract of the invention necessary to achieve the desired therapeutic effect and includes a dose sufficient to reduce a symptom associated with inflammation. Effectiveness in treating inflammation can be determined by observing an improvement in an individual based upon one or more clinical symptoms, and/or physiological indicators associated with the condition. An improvement in inflammation also can be indicated by a reduced need for a concurrent therapy.

The appropriate effective amount of the extract of the invention to be administered to an individual for a particular inflammation can be determined by a person of ordinary skill in the art by taking into account factors, including, without limitation, the type of inflammation, the location of the inflammation, the cause of the inflammation, the severity of the inflammation, the degree of relief desired, the duration of relief desired, the particular dosage of extract of the invention that is used, the rate of excretion of the extract of the invention used, the pharmacodynamics of the extract of the invention used, the nature of other compounds that may be included in the composition, the particular formulation, the particular route of administration, the particular characteristics, history and risk factors of the patient, such as, e.g., age, weight, general health and the like, or any combination thereof.

Additionally, where repeated administration of the extract of the invention is used, an effective amount of the extract of the invention will further depend upon factors, including, without limitation, the frequency of administration, the half-life of the extract of the invention, or any combination thereof.

In the use or method of the invention the extract of the invention may be administered in an amount of from about 100 mg/day to about 2000 mg/day, or from about 500 mg/day to about 1500 mg/day, or about 1000 mg/day. If the extract is administered in the form of a pharmaceutical or veterinary or food, feed or pet food supplement or food, feed or pet food composition comprising the extract, the extract would be present in an amount to provide the above dosages of extract. For example, the food composition may comprise from about 100 mg to about 2000 mg or from about 500 mg to about 1500 mg, or about 1000 mg of the extract of the invention and the pharmaceutical composition may comprise 10 mg, 20 mg, 30 mg, 40 mg, 50 mg, 60 mg, 70 mg, 80 mg, 100 mg, 250 mg, 500 mg, 1000 mg, 1500 mg or 2000 mg of the extract of the invention, such that the food composition or the pharmaceutical or veterinary composition may be administered one or more times per day in order to provide from about 100 mg to about 2000 mg/day or from about 500 mg to about 1500 mg/day, or about 1000 mg/day of the extract of the invention.

When included within a composition (e.g. a pharmaceutical or veterinary composition or a food composition), the extract is typically present in an amount from about 1% by weight to about 100% by weight, for example, from about 10% by weight to about 90% by weight or about 20% by weight to about 80% or from about 30% by weight to about 70% or from about 40% by weight to about 60% by weight.

Pharmaceutical or veterinary or food compositions of the invention may consist of or consist essentially of the extract of the invention and pharmaceutical or veterinary or food composition.

For the avoidance of doubt, in this specification when we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only.

Processes for Obtaining Extracts

The extract of the invention may be obtained from or obtainable from *Rubus idaeus*, in particular, from the arieal parts of *Rubus idaeus*, such as the stem and/or leaves using separation techniques that select for the required extract, which may be determined by those skilled in the art. Seeds and/or fruit may also be present, although it is preferred that that aerial parts of *Rubus idaeus* not including seeds and/or fruit are used.

Typically, the extract of the invention may be obtained by extraction and isolation processes as generally described below, or routine modifications thereof.

For example, the process for providing an extract obtained from *Rubus idaeus* may be described as comprising the steps of:

(a) grinding the aerial part of *Rubus idaeus* (such as the stem and/or leaves) into particles;
(b) contacting the ground particles with a solvent mixture;
(c) separating the ground particles from the solvent mixture, for example by filtration (and optionally repeating step (b) with the separated particles);
(d) evaporating the solvent mixture; and optionally
(e) drying the product obtained in step (d).

Typically, *Rubus idaeus*, such as the arieal part of *Rubus idaeus*, is ground into particles with a diameter in a range from about 0.1 mm to about 30 mm, such as from about 0.5 mm to about 15 mm or from about 1 mm to about 10 mm, e.g. from about 1.5 mm to about 5 mm. Any suitable grinding technique known in the art may used, such as a mesh.

Particular solvents that may be used in the contacting (extraction) process include water, alcohol, alcohol/water mixtures (hydro-alcoholic solvents), ethyl acetate, acetone, hexane or any other solvent that may typically be used for extraction. For example, the extraction solvent may be 10%, 20%, 30%, 40%, 50%, 60%, 70%, 80% or 90% alcohol in water, such as 30% alcohol in water. Particular alcohols that may be mentioned include ethanol (EtOH) and methanol (MeOH). The solvents used may or may not be food grade.

In some instances, the hydro-alcoholic solvent may comprise or consist of from about 30% ethanol to about 70% ethanol, i.e. have a ratio of ethanol/water of from about 30/70 to about 70/30 v/v.

The temperature of the contacting (extraction) step (step (b)) will depend on the solvent used and may be in a range of from about 20° C. to about 150° C. For example, the temperature for extraction may be in a range of from about 50° C. to about 70° C. The temperature for extraction may also be a temperature at which the solvent used for the extraction will reflux.

The contacting (extraction) of *Rubus idaeus* may be performed with or without agitation, such as by maceration.

The contacting (extraction) of *Rubus idaeus* may be performed with or without pressure.

Any suitable extraction apparatus may be used. For example, the extract of the invention may be extracted using Soxhlet apparatus.

Typically, the ratio of plant material to solvent used in the extraction process varies from about 1:1 to about 1:30 on a gram to millilitre basis, such as from about 1:3 to about 1:15 e.g. 1:5 or 1:10 w/v.

The contacting (extracting) period (i.e. the period during which the plant material is in contact with the solvent) is typically from about 0.5 hours to about 24 hours, such as from about 1 hour to about 12 hours. Any un-dissolved plant material may be removed from the solvent, for example, by filtration, and re-dissolved in the solvent. The contacting step may be then be repeated.

The contacting (extraction) step may be repeated more times as deemed necessary. For example, the contacting step may be repeated two, three or four times.

After the plant materials and solvent have been contacted, the solvent may be separated from any un-dissolved plant material (for example, by filtration) and the solvent (filtrate) concentrated (i.e. the solvent is removed) until a solid component has formed. For example, the solvent may be concentrated until all the solvent has been removed and only solid extract remains. Typically, the solvent (filtrate) is concentrated (for example, by rotary evaporation) to about 30% to about 70% DM (Dry Material, Dried Matter or Dry Matter) such as about 50% DM. The resulting solid may be referred to as the "native extract".

The native extract may then be further dried to a % DM of about 90% to about 99%, such as about 97%. Drying processes that may be used include, but are not limited to, atomization, air drying, ovendrying, and sun drying. The drying may be done with or without a carrier, such as those described previously. For example, the drying may be done using maltodextrine as a carrier.

By the process of extraction, certain active compounds within the extract are increased and other compounds decreased when compared to the active compounds found in the originating plant.

The present inventors have found that there is a significant industrial and economic advantage in extracting *Rubus ideaus* in two stages. By including an addition extraction stage, the mass yield is increased without compromising the percentage of active compounds see table below for example.

When using two extraction stages, the mass yield of *Rubus idaeus* extract can be increased by 1.5 compared to when only one extraction is used, while the polyphenol yield is maintained at the same level.

| samples | $H_2O$ 100% two extractions | Water 100% $1^{st}$ extraction | Water 100% $2^{nd}$ extraction | EtOH 30% two extractions | Etoh 30% $1^{st}$ extraction | Etoh 30% $2^{nd}$ extraction |
|---|---|---|---|---|---|---|
| Mass yield (%) | 29.2 | 19.20 | 10 | 27.9 | 19.4 | 8.5 |
| TOTAL Polyphenols by Folin Ciocalteu (%) | 23.48 | 23.42 | 23.68 | 27.23 | 27.15 | 27.52 |

Typically, the resulting solid component may comprise from about 1% to about 40% by weight, such as from about 2% to about 20% or from about 2% to about 15% by weight by weight of phenolic compounds, from about 0.5% to about 7% by weight, such as from about 1% to about 4% by weight of hydroxycimmanic acid and ellagic compounds and from about 1% to about 15% by weight, such as from about 2% to about 6% by weight of flavonoid compounds.

The extract obtained from *Rubus idaeus* may also comprise polyphenols in an amount from about 10% to about 30%, such as from about 15% to about 25% by weight of the extract as calculated using the Folin Ciocalteu method.

Typically, in the process for providing an extract obtained from *Rubus idaeus* (i.e. steps (a) to (e) as described above): the ground particles have a diameter from about 0.1 mm to 30 mm; and/or the temperature is from about 20° C. to about 150° C.; and/or the ratio of ground particles to solvent mixture is from about 1 g to 1 ml to about 1 g to 8 ml; and/or the ground particles are in contact with the solvent mixture from about 0.5 hours to about 24 hours; and/or the solvent mixture is water, a water-alcohol mixture or alcohol.

The terms "isolated" and "purified" as used herein refer to the extract of the invention or compounds within the extract of the invention being separated from at least one other component (e.g. a polypeptide or cellulose derivative) present with the components of the extract in the natural source, e.g. the aerial parts of *Rubus idaeus*. For example, the extract or compounds within the extract may be provided in pure form or in the presence of a solvent, buffer, ion, or other component normally present in a solution of the same.

Thus, the terms "isolated" and "purified" do not refer to the extract or compounds within the extract before they have been extracted from *Rubus idaeus*. Similarly, the term extract refers to components of the natural material having been obtained through a process of extraction, rather than those components before they have been extracted from *Rubus idaeus* (e.g. when present in the aerial parts of *Rubus idaeus*).

The extract of the invention as obtained from such processes may be:
  substantially free of other plant material (e.g. free of plant cellulose);

substantially free of plant cells; and/or
substantially free of plant cellular matter.

As used herein, references to a material being "substantially free" of another material may refer to the material consisting of less than 1% by weight (e.g. less than 0.1%, such as less than 0.01% or less than 0.001%, by weight) of that other material.

The extract of the invention as may be an extract obtained from (or obtainable by) a process of the invention as previously described.

Therapeutic Uses

The extract of the invention may have particular biological effects, which may be useful in the treatment of medical conditions. Thus, according to the present invention, there is provided the use of the extract of the invention for use in treating or preventing inflammation.

Figure 2:
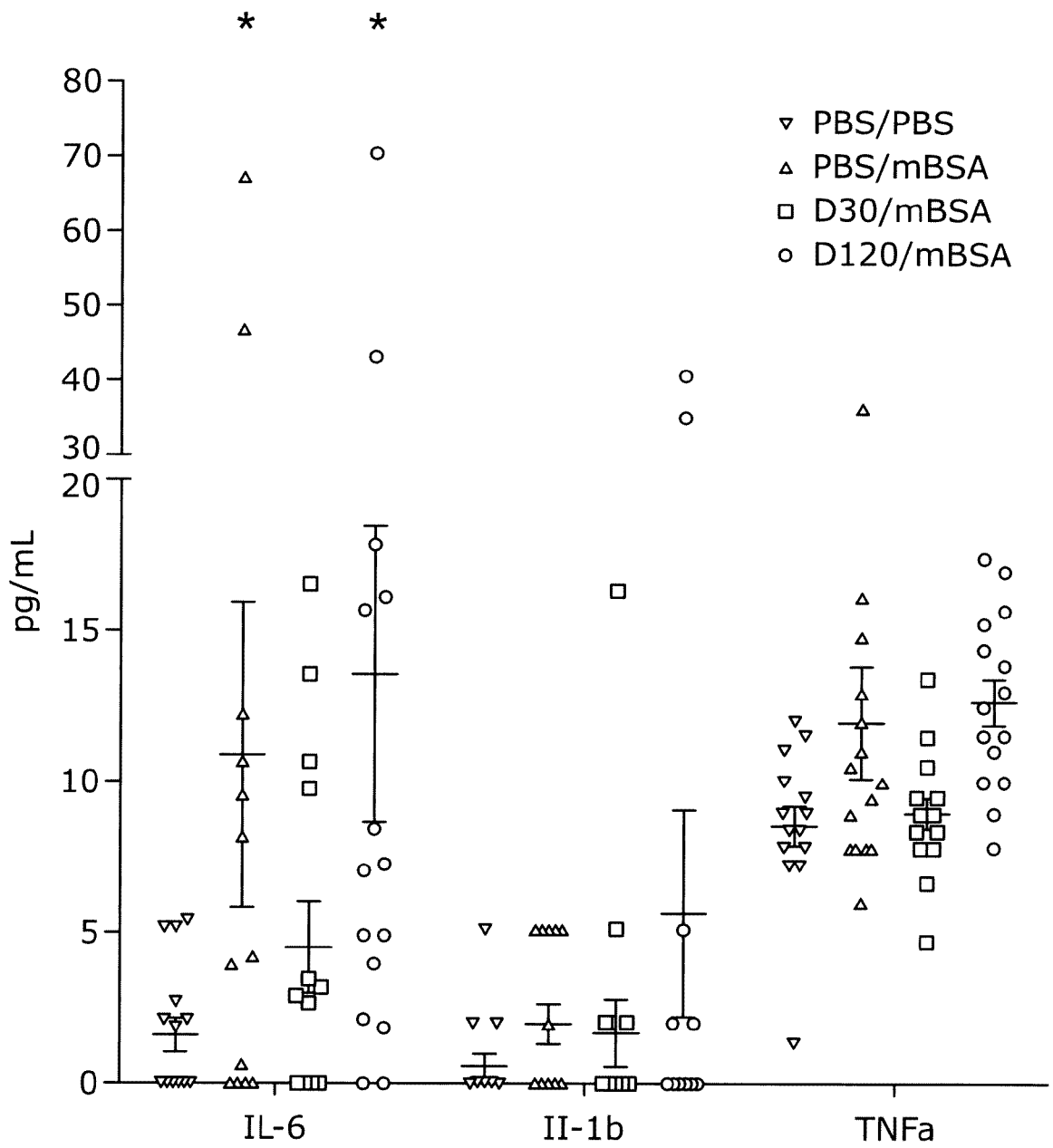
FIG. 2 depicts the plasmatic level of IL-6, IL-1b and TNF-α in treated animals based on the procedure detailed in Example 5.*$P<0.05$ Vs PBS/PBS.

The extract of the invention may reduce and/or inhibit the release of at least one proinflammatory cytokine, such as TNF-alpha, IL-6 and IL-1 beta (as shown in FIG. 2).

Figure 3:
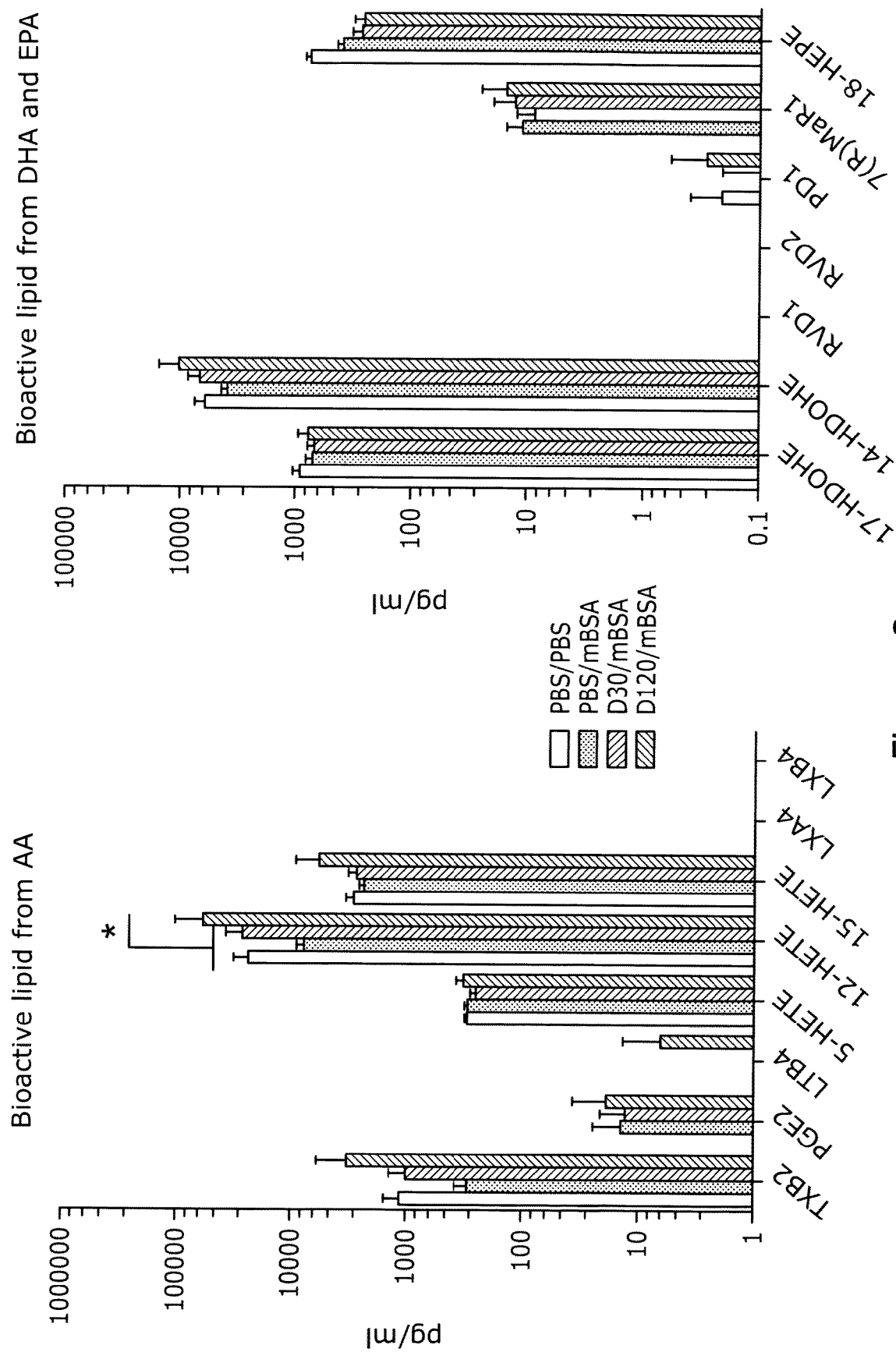
FIG. 3 depicts the plasmatic level of bioactive lipids in treated animals based on the procedure detailed in Example 6. $P<0.05$ Vs D120/mBSA.

The extract of the invention may increase levels of specialised pro-resolving mediators derived from arachidonic acid, eicosapentaenoic acid and/or docosahexaenoic acid (as shown in FIG. 3).

Figure 4:
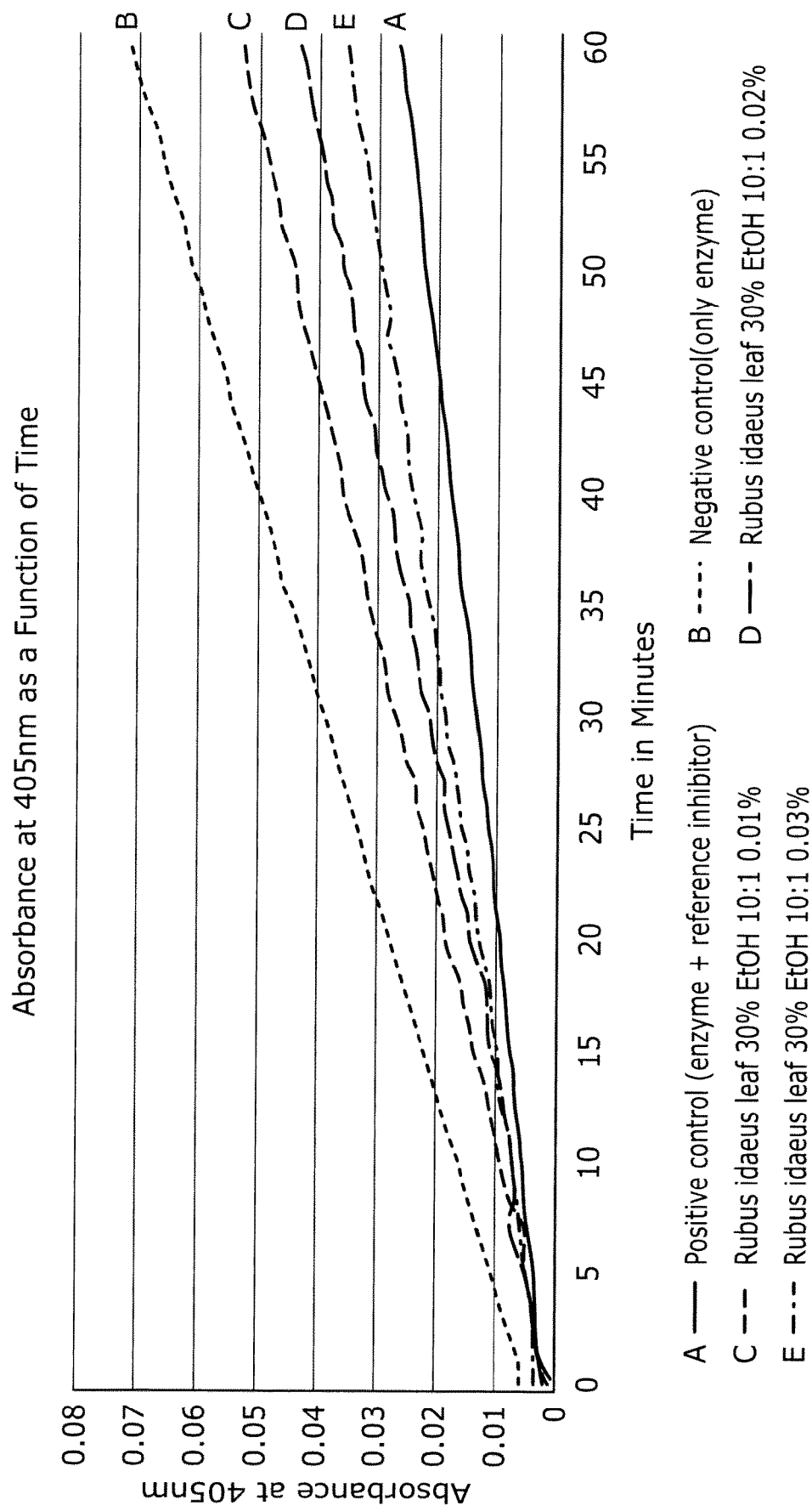
FIG. 4 depicts Granzyme B inhibition for the extract of the invention compared to a positive and negative control.
Figure 5:
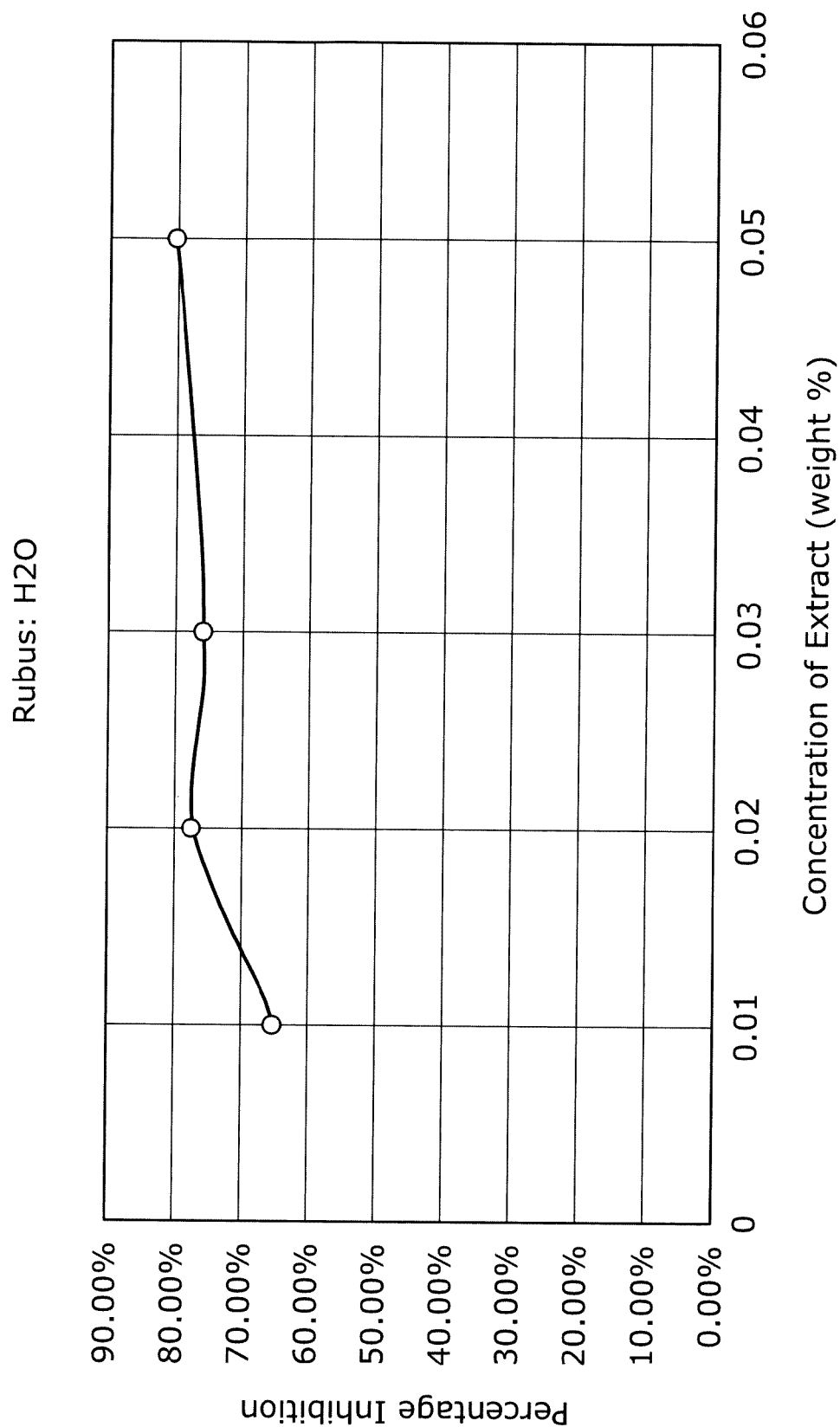
FIG. 5 depicts Granzyme B inhibition for an extract of the invention obtained using water only as the solvent.
Figure 6:
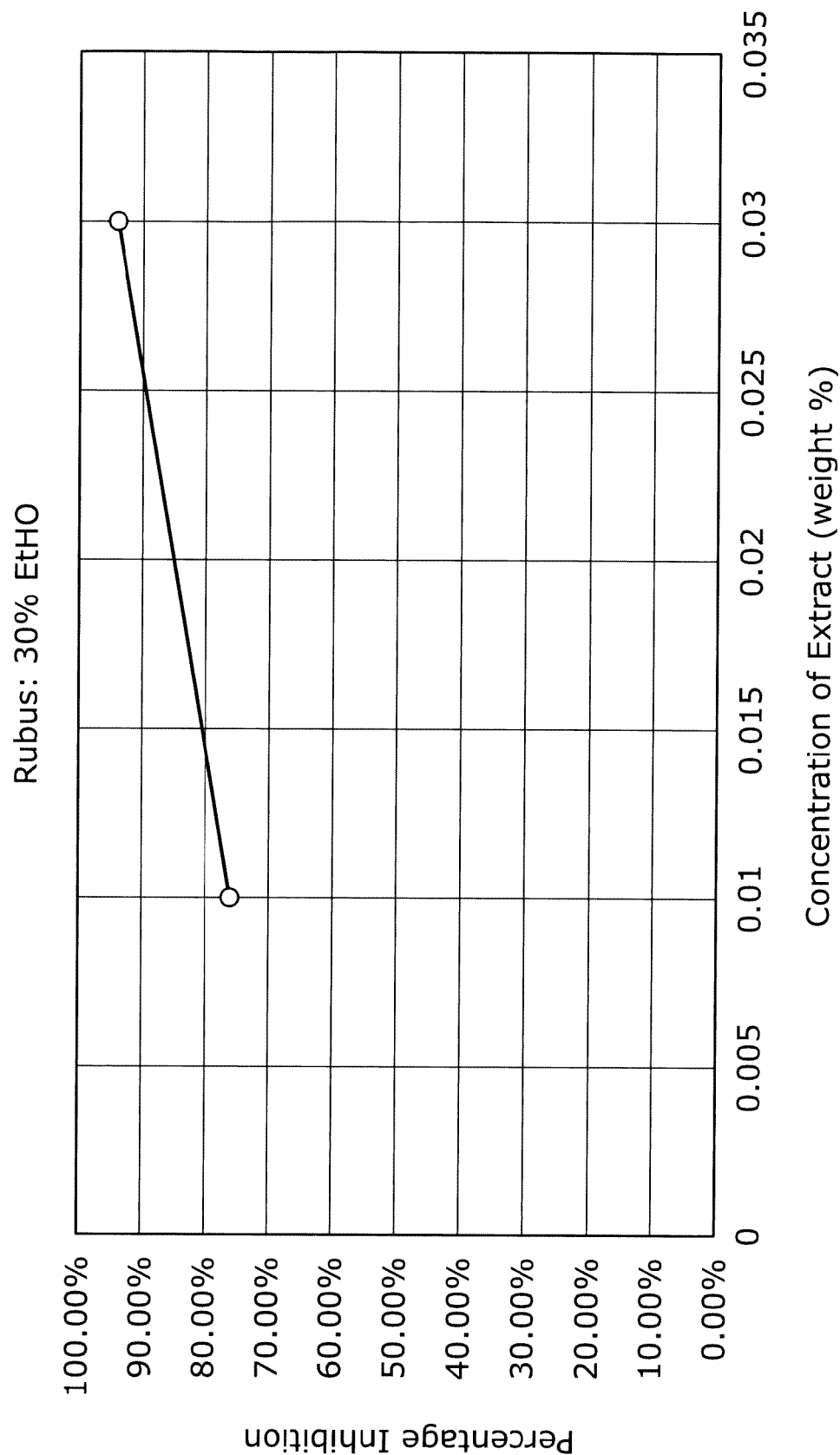
FIG. 6 depicts Granzyme B inhibition for an extract of the invention obtained using a 30% ethanol solvent.

The extract of the invention may inhibit Granzyme B activity (for example, as shown in FIGS. 4, 5 and 6).

Granzyme B is a serine protease that induces cell apoptosis and is involved in apotosis of chondrocytes. Granzyme B also induces cartilage proteoglycan degradation. Serum levels of Granzyme B are increased in conditions such as rheumatoid arthritis and osteoarthritis. Granzyme B-positive cells are present at the invasive front of the pannus tissue in patients with rheumatoid arthritis.

The invention also provides a composition comprising an extract obtained from or obtainable from *Rubus idaeus* for use in treating or preventing inflammation, such as inflammation resulting from rheumatoid arthritis and/or osteoarthritis.

There is also provided the use of an extract obtained from or obtainable from *Rubus idaeus* in the manufacture of a medicament for treating or preventing inflammation, such as inflammation resulting from rheumatoid arthritis and/or osteoarthritis.

There is also provided a method for treating or preventing inflammation, such as inflammation resulting from rheumatoid arthritis and/or osteoarthritis, comprising the administration of a therapeutically effective amount of an extract obtained from or obtainable from *Rubus idaeus* or a composition comprising an extract obtained from *Rubus idaeus* to a subject in need thereof.

Inflammation symptoms can be associated with a large, unrelated group of disorders which underlay a variety of diseases and disorders. The immune system is often involved with inflammatory disorders, demonstrated in both allergic reactions and some myopathies, with many immune system disorders resulting in abnormal inflammation. Non-immune diseases with etiological origins in inflammatory processes that the extract of the invention may be used to treat or prevent include, but are not limited to cancer, atherosclerosis, and ischaemic heart disease. Non-limiting examples of disorders exhibiting inflammation as a symptom include, but are not limited to, acne, acid reflux/heartburn, age related macular degeneration (AMD), allergy, allergic rhinitis, Alzheimer's disease, amyotrophic lateral sclerosis, anemia, appendicitis, arteritis, arthritis, asthma, atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, and vulvitis.

Inflammation as used in the present invention may also comprise tissue inflammation. Tissue inflammation is an inflammation that is confined to a particular tissue or organ. Tissue inflammation that the extract of the invention may be used to treat or prevent includes, but is not limited to skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, stomach inflammation, intestinal inflammation, brain inflammation.

Inflammation may also comprise systemic inflammation. Although the processes involved are typically identical to tissue inflammation, systemic inflammation is not confined to a particular tissue but in fact overwhelms the body, involving the endothelium and other organ systems. When it is due to infection, the term sepsis is applied, with the terms bacteremia being applied specifically for bacterial sepsis and viremia specifically to viral sepsis. Vasodilation and organ dysfunction are serious problems associated with widespread infection that may lead to septic shock and death.

Inflammation as used in the present invention may also comprise an autoimmune disorder. Autoimmune diseases can be broadly divided into systemic and organ-specific autoimmune disorders, depending on the principal clinicopathologic features of each disease. Systemic autoimmune diseases include, without limitation, systemic lupus erythematosus (SLE), Sjogren's syndrome, Scleroderma, rheumatoid arthritis and polymyositis. Local autoimmune diseases may be endocrinologic (Diabetes Mellitus Type 1, Hashimoto's thyroiditis, Addison's disease etc.), dermatologic (pemphigus vulgaris), hematologic (autoimmune haemolytic anemia), neural (multiple sclerosis) or can involve virtually any circumscribed mass of body tissue. Types of autoimmune disorders include, without limitation, acute disseminated encephalomyelitis (ADEM), Addison's disease, an allergy or sensitivity, amyotrophic lateral sclerosis, anti-phospholipid antibody syndrome (APS), arthritis, autoimmune hemolytic anemia, autoimmune hepatitis, autoimmune inner ear disease, autoimmune pancreatitis, bullous pemphigoid, celiac disease, Chagas disease, chronic obstructive pulmonary disease (COPD), diabetes mellitus type 1 (IDDM), endometriosis, fibromyalgia, Goodpasture's syndrome, Graves' disease, Guillain-Barré syndrome (GBS), Hashimoto's thyroiditis, hidradenitis suppurativa, idiopathic thrombocytopenic purpura, inflammatory bowel disease, interstitial cystitis, lupus (including discoid lupus erythematosus, drug-induced lupus erythematosus, lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anaemia, primary biliary cirrhosis, recurrent disseminated encephalomyelitis (multiphasic disseminated encephalomyelitis), rheumatic fever, schizophrenia, scleroderma, Sjögren's syndrome, tenosynovitis, vasculitis, and vitiligo.

Inflammation as used in the present invention may also comprise a myopathy. Myopathies are caused when the immune system inappropriately attacks components of the muscle, leading to inflammation in the muscle. A myopathy includes an inflammatory myopathy and an auto-immune myopathy. Myopathies include, without limitation, dermatomyositis, inclusion body myositis, and polymyositis.

Inflammation as used in the present invention may also comprise a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behcet's disease, or other connective tissue disorders, vasculitis secondary to viral infection.

Inflammation as used in the present invention may also comprise a skin disorder. Skin disorders include, without limitation, an acne, including acne vulgaris, a bullous phemigoid, a dermatitis, including atopic dermatitis and chronic actinic dermatitis, an eczema like atopic eczema, contact eczema, xerotic eczema, seborrhoeic dermatitis, dyshidrosis, discoid eczema, venous eczema, dermatitis herpetiformis, neurodermatitis, and autoeczematization, and statis dermatitis, hidradenitis suppurativa, lichen planus, psoriasis including plaqure psoriasis, nail psoriasis, guttate psoriasis, scalp psoriasis, inverse psoriasis, pustular psoriasis, erythrodermis psoriasis, and psoriatic arthritis, rosacea and scleroderma including morphea.

Inflammation as used in the present invention may also comprise a gastrointestinal disorder. A gastrointestinal disorder includes, without limitation, irritable bowel disease, an inflammatory bowel disease including Crohn's disease and an ulcerative colitis like ulcerative proctitis, left-sided colitis, pancolitis and fulminant colitis.

Inflammation as used in the present invention may also comprise a cardiovascular disease. When LDL cholesterol becomes embedded in arterial walls, it can invoke an immune response. Chronic inflammation eventually can damage the arteries, which can cause them to burst. Cardiovascular disease is any of a number of specific diseases that affect the heart itself and/or the blood vessel system, especially the veins and arteries leading to and from the heart. There are more than 60 types of cardiovascular disorders including, without limitation, a hypertension, endocarditis, myocarditis, heart valve dysfunction, congestive heart failure, myocardial infarction, a diabetic cardiac conditions, blood vessel inflammation like arteritis, phlebitis, vasculitis; arterial occlusive disease like arteriosclerosis and stenosis, inflammatory cardiomegaly, a peripheral arterial disease; an aneurysm; an embolism; a dissection; a pseudoaneurysm; a vascular malformation; a vascular nevus; a thrombosis; a thrombphlebitis; a varicose veins; a stroke. Symptoms of a cardiovascular disorder affecting the heart include, without limitation, chest pain or chest discomfort (angina), pain in one or both arms, the left shoulder, neck, jaw, or back, shortness of breath, dizziness, faster heartbeats, nausea, abnormal heartbeats, feeling fatigued. Symptoms of a cardiovascular disorder affecting the brain include, without limitation, sudden numbness or weakness of the face, arm, or leg, especially on one side of the body, sudden confusion or trouble speaking or understanding speech, sudden trouble seeing in one or both eyes, sudden dizziness, difficulty walking, or loss of balance or coordination, sudden severe headache with no known cause. Symptoms of a cardiovascular disorder affecting the legs, pelvis and/or arm include, without limitation, claudication, which is a pain, ache, or cramp in the muscles, and cold or numb feeling in the feet or toes, especially at night.

Inflammation as used in the present invention may also comprise a cancer. Inflammation orchestrates the microenvironment around tumors, contributing to proliferation, survival and migration. For example, fibrinous inflammation results from a large increase in vascular permeability which allows fibrin to pass through the blood vessels. If an appropriate procoagulative stimulus is present, such as cancer cells, a fibrinous exudate is deposited. This is commonly seen in serous cavities, where the conversion of fibrinous exudate into a scar can occur between serous membranes, limiting their function. In another example, a cancer is an inflammatory cancer like a NF-κB-driven inflammatory cancer.

Inflammation as used in the present invention may also comprise a pharmacologically-induced inflammation. Certain drugs or exogenic chemical compounds are known to affect inflammation. For example, Vitamin A deficiency causes an increase in an inflammatory response. Certain illicit drugs such as cocaine and ecstasy may exert some of their detrimental effects by activating transcription factors intimately involved with inflammation (e.g. NF-κB).

Inflammation as used in the present invention may also comprise an infection. An infectious organism can escape the confines of the immediate tissue via the circulatory system or lymphatic system, where it may spread to other parts of the body. If an organism is not contained by the actions of acute inflammation it may gain access to the lymphatic system via nearby lymph vessels. An infection of the lymph vessels is known as lymphangitis, and infection of a lymph node is known as lymphadenitis. A pathogen can gain access to the bloodstream through lymphatic drainage into the circulatory system. Infections include, without limitation, bacterial cystitis, bacterial encephalitis, pandemic influenza, viral encephalitis, and viral hepatitis (A, B and C).

Inflammation as used in the present invention may also comprise a tissue or organ injury. Tissue or organ injuries include, without limitation, a burn, a laceration, a wound, a puncture, or a trauma.

Inflammation as used in the present invention may also comprise a transplant rejection. Transplant rejection occurs when a transplanted organ or tissue is not accepted by the body of the transplant recipient because the immune system of the recipient attacks the transplanted organ or tissue. An adaptive immune response, transplant rejection is mediated through both T cell mediated and humoral immune (antibodies) mechanisms. A transplant rejection can be classified as a hyperacute rejection, an acute rejection, or a chronic rejection. Chronic rejection of a transplanted organ or tissue is where the rejection is due to a poorly understood chronic inflammatory and immune response against the transplanted tissue. Also included in the term "transplant rejection" is a graft-versus-host disease (GVHD). GVHD is a common complication of allogeneic bone marrow transplantation in which functional immune cells in the transplanted marrow recognize the recipient as "foreign" and mount an immunologic attack. It can also take place in a blood transfusion under certain circumstances. GVHD is divided into acute and chronic forms. Acute and chronic GVHD appear to involve different immune cell subsets, different cytokine profiles, somewhat different host targets, and respond differently to treatment.

Inflammation as used in the present invention may also comprise a Th1-mediated inflammatory disease. In a well-functioning immune system, an immune response should result in a well balanced pro-inflammatory Th1 response and anti-inflammatory Th2 response that is suited to address the immune challenge. Generally speaking, once a pro-inflammatory Th1 response is initiated, the body relies on the anti-inflammatory response invoked by a Th2 response to counteract this Th1 response. This counteractive response includes the release of Th2 type cytokines such as, e.g., IL-4, IL-5, and IL-13 which are associated with the promotion of IgE and eosinophilic responses in atopy, and also IL-10, which has an anti-inflammatory response. A Th1-mediated inflammatory disease involves an excessive pro-inflammatory response produced by Th1 cells that leads to chronic inflammation. The Th1-mediated disease may be virally, bacterially or chemically (e.g. environmentally) induced. For example, a virus causing the Th1-mediated disease may cause a chronic or acute infection, which may cause a respiratory disorder or influenza.

The extract of the invention or composition comprising an extract of the invention is typically administered to an individual, for example a human or an animal subject.

Animal subjects that may be treated by the extract or composition of the invention include, but are not limited to, cats, dogs, horses, and cattle (such as sheep and cows).

The disease or disorder to be treated or prevented is typically selected from the group(s) consisting of osteoarthritis (OA), rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

Arthritis is a heterogeneous disease that induces whole-joint damage, such as that found in osteoarthritis (OA). OA is characterized by inflammation of the synovial membrane, modification of the subchondral bone and degradation of the cartilage. Chondrocytes degenerating to hypetrophic chondrocyte until apoptosis will participate along with synovial and immune cells, to secrete prostaglandins and interleukin 1beta (IL1b) leading do cartilage catabolism. Once homeostasis is disrupted, matrix degradation becomes inevitable. Indeed, overexpression of matrix metalloproteinases (MMPs) and metalloproteinase with thrombospondin motifs (ADAMTS), as well as a decrease in the tissue inhibitor of metalloproteinases (TIMPs) will degrade the matrix. Furthermore, the overexpressed cytokines inducing an increased production of nitric oxide (NO), prostaglandin E2 (PGE2) and leukotrienes will provoke chondrocyte apoptosis. Cartilage matrix degradation products will then be released into the synovial fluid and will exacerbate inflammation, leading to infiltration of innate immune cells into joint tissues (synovium and IFP) and secretion of inflammatory mediators. All these mechanisms of action will lead to advanced OA, in which articular cartilage loss is initiated via fibrillation of the superficial zone followed by cartilage damage.

As used herein, the term "treatment" (and, similarly, "treating") takes its normal meaning in the field of medicine. In particular, the term may refer to achieving a reduction in the severity of one or more clinical symptom associated with the disease or disorder (e.g. the fungal infection), as may be determined using techniques known to those skilled in the art (for example, by a medical physician) and/or to slowing the progression of the disease or disorder (i.e. increasing the amount of time taken for the disease or disorder to progress to a more severe state, e.g. when compared to the time expected to be taken in a patient not so treated).

As used herein, the term "prevention" (and, similarly, "preventing") includes references to the prophylaxis of the disease or disorder (and vice-versa). In particular, the term may refer to achieving a reduction in the likelihood of the patient (or healthy subject) developing the condition (for example, at least a 10% reduction, such as at least a 20%, 30% or 40% reduction, e.g. at least a 50% reduction).

For the avoidance of doubt, in the context of the present invention, the terms "treating" and "preventing" include the therapeutic, or palliative, treatment of subjects/patients in need of, as well as the prophylactic treatment and/or diagnosis of patients which are susceptible to, the relevant disease states.

As used herein in relation to medical conditions, the term "reducing" may refer to making the observed quantity smaller or decrease in size.

As used herein, the terms "subject" and "patient" may be used interchangeably and include mammalian species (particularly humans).

EXAMPLES

The present invention will be further described by reference to the following, non-limiting examples.

Example 1: Typical Extraction of Rubus idaeus Extract

The extract of the invention is typically prepared as follows:

Rubus idaeus (aerial part: leaves/stems) was ground so that the particles could fit through a 4 mm mesh and the ground material mixed with EtOH/water (30% ethanol in water) in a reactor. The ratio of solvent: plant material was 10:1 (v/w). The raw material was then extracted under reflux with agitation for about 1 hour 30 minutes.

After the extraction, the mixture was filtered using a filter of 25 micron in order to separate the liquid from the solid phase (cake).

The extraction step was repeated, and the resulting filtrates combined. The solid phase was discarded.

The combined filtrates were then concentrated under vacuum (e.g. 0.8 Pa) to 50% DM.

The resulting extraction solid was referred to as the "native extract."

The native extract was then spray dried to a % DM content of about 97%.

Example 2: Determination of Total Phenol, Sanguiin H6 and Lambertiannin C Dosage in Rubus idaeus Extract The amount of various compounds, including phenolic compounds such as ellagitannins, lambertianin C and sanguiin h6, ellagic acid compounds such as chlorogenic acid and allagic acid, flavonoids compounds such as quercetin-3-O-xyl-glucoronide, hyperoside, quercetin and kaempferol were determined in Rubus idaeus extract using the following HPLC method.

Quantification of target compounds was performed on an HPLC Agilent 1100 HPLC system equipped with a UV detector. The separation of compounds was carried out on Atlantis T3 $C_{18}$ 150 mm×3.0 mm; 3 μm set at 32° C. The mobile phase consisted of acetonitrile/water (50:50) +0.1% formic acid (eluent A) and water+0.1% formic acid (eluent B).

The gradient for eluent A was as follow: 0 min, 12%; 10 min, 20%; 30 min, 43%; 40 min, 100%; 55 min, 100%.

The gradient for eluent B was the difference between 10% and eluent A gradient.

The total run time was 50 mm Injection volume was 2 μL and flow rate was 0.6 mL/min.

UV monitoring was performed at 280 nm for phenolic compounds detection, 325 nm for ellagic compounds detection and 348 nm for flavonoids compounds. The amount of target compounds were quantified by comparing peak area of the sample with peak area of reference compound of known concentration.

The total phenolic content were determined by using the Folin-Ciocalteu assay as described in Singleton, V. L., & Rossi, J. A. (1965). Colorimetry of total phenolics with phosphomolybdic-phosphotungstic acid reagents. *American journal of Enology and Viticulture*, 16(3), 144-158.

TABLE 1 the analytic results of an aqueous rubus Idaeus extract and a rubus Idaeus extract obtained using 30% ethanol in water.

| Compounds | $t_R$ (min) | EtOH 30% | $H_2O$ 100% |
|---|---|---|---|
| Phenolics compounds 280 nm | | | |
| Ellagitannin C68H48O44* | 5.21 | 0.21 | 0.13 |
| Ellagitannin C68H48O44* | 6.62 | 0.05 | 0.05 |
| Ellagitannin C68H48O44* | 7.3 | 0.23 | 0.22 |
| Ellagitannin C68H48O44* | 8.36 | 0.31 | 0.24 |
| Ellagitannin C68H48O44* | 12 | 0.26 | 0.07 |
| Ellagitannin C68H48O44* | 14.1 | 0.09 | 0.02 |
| Ellagitannin C68H48O44* | 14.54 | 0.1 | 0.04 |
| Geraniin | 15.47 | 0.02 | |
| Ellagitannin C68H48O44* | 16.64 | 0.13 | 0.003 |
| Ellagitannin C68H48O44* | 17.26 | 0.19 | |
| Ellagitannin C68H48O44* | 18.42 | 0.35 | 0.17 |
| Sanguiin H10* | 18.84 | | 0.003 |
| Ellagitannin C68H48O44* | 19.77 | 0.33 | |
| Ellagitannin C68H48O44* | 20.41 | 0.4 | 0.3 |
| Ellagitannin C68H48O44* | 20.71 | 0.16 | 0.17 |
| Ellagitannin C68H48O44* | 21.19 | 0.16 | 0.01 |
| Lambertianin C* | 21.75 | 2.49 | 0.66 |
| Sanguiin H6* | 22.41 | 4.52 | 1.37 |
| TOTAL (%) | | 10.00 | 3.46 |
| Hydroxycinnamic acid and ellagic acid compounds 325 nm | | | |
| Chlorogenic acid | 5.66 | 0.05 | 0.05 |
| Chlorogenic acid | 7.81 | 0.11 | 0.12 |
| Chlorogenic acid | 9.05 | 0.06 | 0.07 |
| Chlorogenic acid | 9.4 | 0.1 | 0.09 |
| Chlorogenic acid | 9.87 | 0.05 | 0.05 |
| Chlorogenic acid | 10.42 | 0.05 | |
| Chlorogenic acid | 11.62 | 0.32 | 0.3 |

TABLE 1-continued the analytic results of an aqueous rubus Idaeus extract and a rubus Idaeus extract obtained using 30% ethanol in water.

| Compounds | $t_R$ (min) | EtOH 30% | $H_2O$ 100% |
|---|---|---|---|
| p-coumaric acid | 12.92 | 0.09 | 0.14 |
| Chlorogenic acid | 14.98 | 0.12 | 0.18 |
| Ellagic acid | 24.69 | 0.49 | 0.27 |
| Ellagic acid | | 1.44 | 1.27 |
| Flavonoids compounds 348 nm | | | |
| Quercetin-3-O-xyl-glucuronide | 23.03 | 0.22 | 0.24 |
| Hyperoside | 24.69 | 0.35 | 0.21 |
| Kaempferol glucoside | 25.57 | 0.21 | 0.18 |
| Quercetin-3-O-glucuronide | 26.14 | 1.06 | 1 |
| Quercetin C27H28O16 | 27.53 | 0.45 | 0.41 |
| Kaempferol glucoside | 29.49 | 0.55 | 0.52 |
| Kaempferol 3-O-glucuronide | 30.16 | 0.25 | 0.23 |
| Kaempferol 3-O-galactoside | 30.68 | 0.13 | 0.12 |
| TOTAL (%) | | 3.22 | 2.91 |
| % polyphenols by folin Ciocalteu method | | | |
| H20 100% | | 19.07 | |
| EtOH 30% | | 23.11 | |

*refers to different ellagitannin compounds from the same family

Example 3: The Effect of *Rubus idaeus* on the Resolution Phase of Inflammation Peripheral blood mononuclear cells (PBMCs) were seeded and allowed to sediment for 1 h. After 1 h, *Rubus idaeus* extract was added and incubated for an extra hour. At the end of this time, an inflammatory response was induced by PMA/A23187 in presence of PUFA (DHA/EPA at 1 µg/ml each), the reaction time was for 1 hour. The culture supernatants were then removed for analysis of the lipid mediators.

Each supernatant was concentrated by solid phase extraction (SPE) and analyzed in LC/MS. An analytical method by coupling liquid chromatography and mass spectrometry (LC/MS) was used in order to quantify the bio-active lipids. The LC/MS analyzes were performed on an LC 1290 Infinity (Agilent Technologies) chain coupled to a 6460 Triple Mass Spectrometer Quad LC/MS (Agilent Technologies) equipped with an electrospray ionization source (Jet stream technology) operating in the negative world. The chromatographic separations were carried out on a ZorBAX SB-C18 column (2.1×50 mm*1.8 µm).

As shown in Table 2, the analysis revealed that the *Rubus idaeus* extract increases the secretion of 5-HETE and 12-HETE, intermediaries of lipoxins synthesis implicated into the resolution of inflammation.

Example 4: The Effect of *Rubus idaeus* Extract on Joint Swelling Animal Model of Arthritis This study was designed to evaluate the ability of *Rubus idaeus* extract to treat the inflammatory process involved in an arthritis mBSA animal model.

The protocol and more particularly the animal model described below, was based on the publication reference Y H Yang et al, Arthritis and Rheumatism, 2004, in which the authors studied the effect of a receptor agonist of the resolution.

The mice used in these experiments were 6 weeks old C57/BL6 females. They were divided in cages of 3 animals and subjected to a normal diet (Safe—ref A04 which guaranty 16.1% of protein, 3.1% fat, 5.1% ashes and 3.9% cellulose for a total of 2.9 kcal/g eaten) and fluid intake ad libitum throughout the experiment. Before the experiment, they had undergone a phase of acclimatization.

Two weeks before the first induction of mBSA, and throughout the duration of the experiment, the mice were divided into 4 groups and received (i) PBS/PBS (negative control); (ii) PBS/mBSA (positive control); (iii) a treatment of 30 mg/Kg of *Rubus Idaeus* extract (D30/mBSA) or (iv) a treatment of 120 mg/Kg of *Rubus idaeus* extract (D120/mBSA). Treatments were administered by gavage once per day.

Induced arthritis methylated albumin (mBSA) was developed in the mice. Induction to mBSA consists in carrying out a first immunization by the mBSA to 1 mg/ml in complete

TABLE 2 the effect of Rubus idaeus extract on the mechanism of resolution of inflammation.

| | Dose | PGE2 | 18-HETE | 15-HETE | 17-HDOHE | 14-HDOHE | 12-HETE | 5-HETE |
|---|---|---|---|---|---|---|---|---|
| Ctrl PBMC | | −91.2 | −100 | −71.5 | −98 | −76.9 | −78.6 | −99.7 |
| PMA/A23187 + AGPI | | 0.0 | 0.0 | 0.0 | 0.0 | 0.0 | 0.0 | 0.0 |
| Rubus Idaeus | 20 µg/ml | −2.8 | 8.8 | −0.9 | 3.3 | 2.6 | 11.7 | 23.6 |

Freud's adjuvant with subcutaneous injection (200 µl). A week later, the animals were again injected with a cocktail of the same composition in the tail (100 µl) and arthritis was induced two weeks after using a 10 µl injection of mBSA (3 mg/ml diluted in PBS) or PBS alone as a control directly in each of the joints of the back legs. All injections were performed under general anesthesia with Vetoflurane.

After injection of mBSA into the joint of the hind legs, their swelling was measured using calipers at 2, 4, 6, 24, 48 and 72 hours post injection. The measurement was taken at the width and thickness of the paw of the animal.

The results showed that mBSA injection induced an increase in paw thickness which became significantly different from the control paws (PBS/PBS). The increase was visible 24 hours after injection up to 72 hours (end of measurement).

After 6 hours, 120 mg of *Rubus Idaeus* extract significantly reduced the paws thickness compared to PBS/mBSA group. Overall, when mice are force-fed with *Rubus idaeus* extract, the thickness of the lower paws was not significantly different than the paws thickness of the PBS/PBS nor than the positive control one (PBS/mBSA). Therefore, as shown in FIG. 1, *Rubus idaeus* extract prevents the appearance of the inflammation by reducing its virulence.

These results demonstrated a beneficial effect of *Rubus idaeus* extract on the articular swelling.

Example 5: The Effect of *Rubus idaeus* Extract on IL-6, IL-1b and TNF-a Plasmatic Level in Animal Model of Arthritis Using the same animals as in Example 4, 72 h after the *Rubus idaeus* injection and before euthanasia, blood was sampled at the renal artery using a sterile syringe without endotoxins. Plasma was separated and samples were then frozen for subsequent analysis.

The cytokine analysis was performed using the Luminex 100IS camera. This device is designed to the acquisition and analysis of microdosing multiplex tests, which uses Luminex xMAP technology (Multi Profiling Analysis) with microspheres different fluorescence, allowing simultaneous quantification up to 100 parameters in a single well in a microvolume. The cytokines of interest were: IL-6, IL-1b and TNF-α which are known to play a central role in joint disorders.

The results demonstrated that PBS/mBSA animals have a level of IL-6 in plasma statistically higher than the control animals PBS/PBS as well as a higher amount of IL-1b and TNF-α.

As shown in FIG. 2, *Rubus idaeus* extract reversed the inflammatory process. Indeed, D30/mBSA prevented the released of the statistically significant increase of IL-6 as measured in PBS/mBSA compared to PBS/PBS. *Rubus idaeus* extract also had a tendency to reduce TNF-a levels.

These results demonstrated an anti-inflammatory effect of the *Rubus idaeus* extract.

Example 6: The Effect of *Rubus idaeus* Extract on Bioactive Lipid Compounds Plasmatic Level in Animal Model of Arthritis Using the same animal as in Example 4, blood sample were analyzed to measure the bioactive compounds level from arachidonic acid (AA), eicosapentaenoic acid (EPA) and docosahexanoic acid (DHA) which are clearly identify into the resolution of inflammation.

Plasmas were thawed on ice and the lipid compounds were concentrated by solid phase extraction (SPE), taken up in methanol before spectrometric analysis. The analytical method used consists in separating the various analytes by high pressure liquid chromatography depending of their retention time and to quantify them by mass spectrometry.

Analysis was carried out on an LC 1290 Infinity chain (Agilent Technologies) coupled with a 6460 Triple Quad LC/MS (Agilent Technologies) mass spectrometer equipped with an electrospray ionization source (Jet stream technology) operating in a negative world. Chromatographic separations were performed on a Zorbax SB-C18. According to the method described by Baillif et al. In: LC-MS/MS method for rapid and concomitant quantification of pro-inflammatory and pro-resolving polyunsaturated fatty acid metabolites. J Chromatogr B Analyt Technol Biomed Life Sci. 2013; 932: 123-33.

The results (as shown in FIG. 3) showed that 12-HETE level after *Rubus idaeus* intake was statistically significantly increased compared to PBS/mBSA. Furthermore, *Rubus idaeus* intake restored, baseline level of 14-HDOHE and 7 (R) MAR1 in sick animals compared to PBS/mBSA. Both of these lipids are secondary metabolite from DHA degradation which are responsible to promote phagocytosis of particles apoptotic inflammatory macrophages.

14-HDOHE is a precursor of the 7 (R) MAR1 and 7 (R) MAR1 and is described as one of the most effective agents in the resolution in particular by promoting phagocytosis of particles apoptotic inflammatory macrophages. Therefore, the return to basal endogenous production rate indicates that the *Rubus idaeus* can trigger the natural ability to produce these molecules to fight inflammation, which is the foundation of the concept of resolution.

Example 7: The Effect of *Rubus idaeus* Extract on Joint Histological Inflammation in Animal Model of Arthritis Using the same animals as used in Example 4, this experiment was set up to determine whether the changes observed in the paw swelling as well as in cytokines and bioactive lipids secretion, could lead to improved tissue parameters. To do so right legs joints of the animals were collected, microtomed and stained to evaluate the histological lesions.

Figure 7:
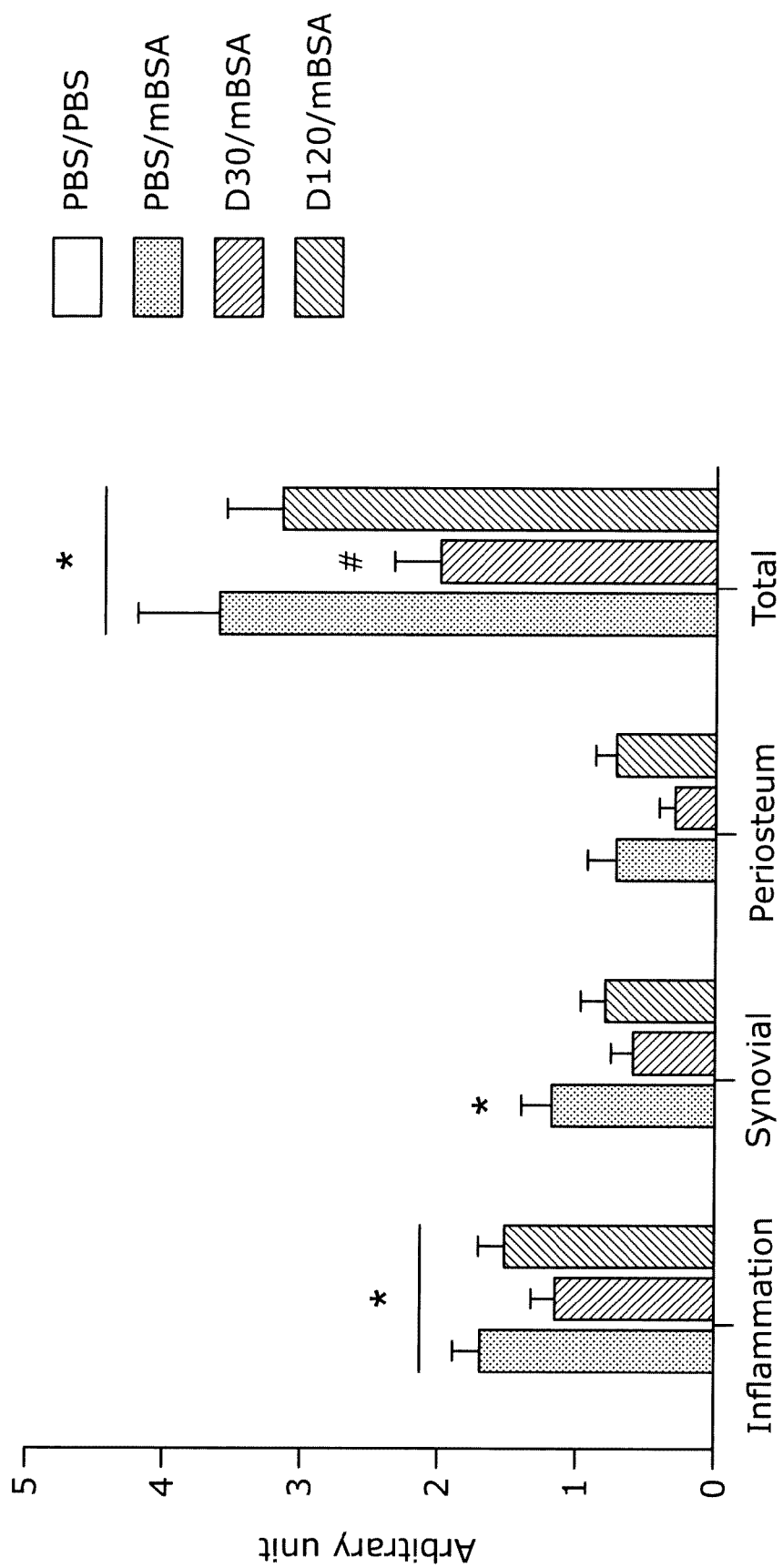
FIG. 7 depicts the histological results of right leg tissues based on the procedure detailed in Example 7.*$P<0.05$ vs PBS/PBS; #$P<0.05$ vs PBS/mBSA.

The results (as shown in FIG. 7) demonstrated a statically significant increased inflammation with penetration of lymphocytes, plasma cells, polymorphonuclear neutrophils and histiocytes in all the PBSA-treated animals. The synovial membrane was also statistically significantly marked with increased inflammation in PBSA-treated animal, which was not the case when treated with *Rubus idaeus* extract and more specifically with at a dose of 30 mg/Kg (D30/mBSA) and 120 mg/Kg D120/mBSA, demonstrating a preventive effect of *Rubus idaeus* extract on the synovial inflamation. In the periosteum a tendency of increased inflammation was observed in all the mBSA treated group. Results on the overall inflammation revealed that animals treated with *Rubus idaeus* extract showed a statically significant decrease score compared to PBSA-treated animals.

Example 8: The Effect of *Rubus idaeus* Extract Inflammatory Response on Chondrocytes Stimulated by IL1

Chondrocytes were extracted from tibia and femoral epiphyses and femoral heads of 5-6 day old mice (C57B1/6 strain). The isolation of chondrocytes from the cartilaginous matrix was achieved by the action of the libertase (100 µg/ml, Roche Applied Science) for 24 hours. The cells were then seeded at a density of 200,000 cells/ml in 12-well plates at a rate of 1 mL per well as a duplicate cultured in DMEM medium (Gibco®, Invitrogen) supplemented with 10% FCS, 2% Glutamine (Gibco®, Invitrogen) and 1% penicillin/streptomycin.

After confluence of the chondrocytes (4-6 days of culture), the latter were cultured in medium without SVF 24 h, activated by IL1 (1 ng/ml) 24 h and then cultured in the presence of one of the 4 concentrations (10 µg/mL, 20 µg/mL, 40 µg/mL or 100 µg/mL) of 30% ethanolic *Rubus idaeus* extracts or aqueous *Rubus idaeus* extract or 5/50 of both extracts for an additional 24 h. These doses were defined in preliminary experiments evaluating the impact of extracts on markers of inflammation from peripheral blood mononuclear cells (PBMC) such as described into example 2.

At the end of the culture (IL1 24 h and 24 h with the *Rubus idaeus* extracts), several experiments will be performed to analyze gene or protein expression.

For gene expression, the chondrocyte cultures were stopped by Trizol and RNA extraction was performed to analyze gene expression by quantitative PCR markers of catabolic (MMP3, MMP13, ADAMTS4, Adamts5), anabolic markers (Collagen Type 2, Aggrecan, Sox9), hypertrophy markers (collagen X, VEGF) and inflammation (COX2).

These experiments were repeated for a cell survival assay using the MTT assay (3-(4,5-dimethylthiazol-2-yl) -2,5-diphenyl tetrazolium) and to test apoptosis by TUNEL (Apoptag, Apoptosis Detection Kit (Millipore)).

Example 9: Inhibition of Granzyme B

The activity of Granzyme B was tested over time in the presence of 0.03% *Rubus idaeus* 30% ethanol extract, 0.02% *Rubus idaeus* 30% ethanol extract, 0.01% *Rubus idaeus* 30% ethanol extract, and a known Granzyme B inhibitor (positive control). A negative control was also set up.

As shown in FIG. 4, each of the *Rubus* extracts inhibited the activity of Granzyme B.

Example 10: Comparison of Granzyme B Inhibition Between an Aqueous Rubus Extract and a 30% Ethanolic Extract The inhibitory activity of a 0.01% and a 0.03% *Rubus idaeus* extract obtained using 30% ethanol was compared to the inhibitory activity of a 0.01%, 0.02%, 0.03% and 0.05% *Rubus idaeus* extract obtained using water only as the solvent.

As shown in FIGS. 5 and 6, the activity of the extract obtained using 30% ethanol was significantly higher than the activity of the extract obtained using water only.

The invention claimed is:

1. A method for treating or preventing inflammation comprising:
   administering to a subject in need thereof a therapeutically effective amount of an extract obtained from the stems and/or the leaves of *Rubus idaeus*, wherein the extract is obtained using water and/or ethanol as the extraction solvent, and wherein the inflammation is associated with arthritis or joint swelling, and wherein the extract comprises:
   (i) from about 1% to about 40% by weight of phenolic compounds;
   (ii) from about 0.5% to about 7% by weight of hydroxycimmanic acid and ellagic compounds; and
   (iii) from about 1% to about 15% by weight of flavonoid compounds.

2. The method according to claim 1, wherein the treating or preventing inflammation reduces joint degeneration.

3. The method according to claim 1, wherein the method reduces and/or inhibits the release of at least one proinflammatory cytokine.

4. The method according to claim 3, wherein the at least one proinflammatory cytokine is selected from TFN-alpha, IL-6, and IL-1-beta.

5. The method according to claim 1, wherein the method increases levels of specialised pro-resolving mediators derived from arachidonic acid, eicosapentaenoic acid and/or docosahexaenoic acid.

6. The method according to claim 1, wherein the extract is administered in the form of a pharmaceutical or veterinary composition comprising the *Rubus idaeus* extract and optionally a pharmaceutically or veterinary acceptable excipient.

7. The method according to claim 6, wherein the pharmaceutical composition is for oral, rectal, nasal, pulmonary, buccal, sublingual, transdermal, intracisternal, intraperitoneal, or parenteral administration.

8. The method according to claim 1, wherein the extract is in the form of a food, feed or pet food composition or product, a drink product or a food, feed or pet food supplement comprising the *Rubus idaeus* extract and optionally food or drink acceptable ingredients.

9. The method according to claim 1, wherein the extract is administered in an amount from about 10 mg/day to about 2000 mg/day.

10. The method according to claim 1, wherein the subject is a human subject.

11. The method according to claim 1, wherein the extract is obtained exclusively from the stems and/or the leaves of *Rubus idaeus*.

12. The method according to claim 1, wherein the arthritis is rheumatoid arthritis and/or osteoarthritis.

* * * * *